(12) United States Patent
Falkowski et al.

(10) Patent No.: US 12,172,146 B2
(45) Date of Patent: Dec. 24, 2024

(54) METAL-ORGANIC FRAMEWORK MATERIALS COMPRISING A PYRAZOLYLBENZOATE LIGAND AND METHODS FOR PRODUCTION THEREOF

(71) Applicant: ExxonMobil Technology and Engineering Company, Annandale, NJ (US)

(72) Inventors: Joseph M. Falkowski, Hampton, NJ (US); Yogesh V. Joshi, Bridgewater, NJ (US); Mary S. Abdulkarim, Palisades Park, NJ (US); Simon C. Weston, Annandale, NJ (US)

(73) Assignee: EXXONMOBIL TECHNOLOGY AND ENGINEERING COMPANY, Spring, TX (US)

( * ) Notice: Subject to any disclaimer, the term of this patent is extended or adjusted under 35 U.S.C. 154(b) by 469 days.

(21) Appl. No.: 17/607,168

(22) PCT Filed: May 26, 2020

(86) PCT No.: PCT/US2020/034486
§ 371 (c)(1),
(2) Date: Mar. 23, 2022

(87) PCT Pub. No.: WO2021/002982
PCT Pub. Date: Jan. 7, 2021

(65) Prior Publication Data
US 2022/0305456 A1    Sep. 29, 2022

Related U.S. Application Data

(60) Provisional application No. 62/870,188, filed on Jul. 3, 2019.

(51) Int. Cl.
*B01J 20/22* (2006.01)
*B01J 20/28* (2006.01)
(Continued)

(52) U.S. Cl.
CPC ....... *B01J 20/226* (2013.01); *B01J 20/28066* (2013.01); *B01J 20/28073* (2013.01);
(Continued)

(58) Field of Classification Search
CPC ............... B01J 20/226; B01J 20/28066; B01J 20/28073; B01J 20/28076; B01J 20/2808;
(Continued)

(56) References Cited

PUBLICATIONS

Janiak et al. ("Bifunctional pyrazolate-carboxylate ligands for isoreticular cobalt and zinc MOF-5 analogs with magnetic analysis of the {Co4(μ4-O)} node", CrystEngComm, 2013, 15, 9757-9768. (Year: 2013).*

(Continued)

*Primary Examiner* — Ali Z Fadhel
(74) *Attorney, Agent, or Firm* — Shook, Hardy & Bacon L.L.P.

(57) ABSTRACT

Metal-organic framework materials (MOFs) are highly porous entities comprising a multidentate organic ligand coordinated to multiple metal centers, typically as a coordination polymer. Some highly porous MOFs lack stability at ambient conditions. MOFs having ambient condition stability may comprise a plurality of metal clusters ($M_4O$ clusters, M=a metal), and a plurality of 4-(1H-pyrazol-4-yl) benzoate ligands coordinated to the plurality of metal clusters to define an at least partially crystalline network structure having a plurality of internal pores. Methods for synthesizing these MOFs may comprise combining a metal source, such as a preformed metal cluster, with 4-(1H-pyrazol-4-yl)benzoic acid, and reacting the preformed metal cluster with the 4-(1H-pyrazol-4-yl)benzoic acid to form a MOF having an at least partially crystalline network structure with a plurality of internal pores defined therein and comprising a plurality of metal clusters coordinated to a multidentate organic ligand comprising 4-(1H-pyrazol-4-yl) benzoate.

13 Claims, 4 Drawing Sheets

(51) Int. Cl.
*C07C 7/12* (2006.01)
*C07F 3/06* (2006.01)

(52) U.S. Cl.
CPC ..... *B01J 20/28076* (2013.01); *B01J 20/2808* (2013.01); *B01J 20/28083* (2013.01); *C07C 7/12* (2013.01); *C07F 3/06* (2013.01)

(58) Field of Classification Search
CPC ... B01J 20/28083; B01J 20/3285; C07C 7/12; C07F 3/06; C08G 83/008
See application file for complete search history.

(56) References Cited

PUBLICATIONS

Dechnik, J. et al. (2017) "Mixed-Matrix Membranes of the Air-Stable MOF-5-Analogue [$Co_4(\mu_4$-O)($Me_2$pzba)$_3$] with a Mixed-Functional Pyrazolate-Carboxylate Linker for $CO_2$/$CH_4$ Separation," *Cryst. Growth Des.*, v.17, pp. 4090-4099.
Gordon, R. M. et al. (1983) "Preparation and properties of tetrazinc μ4-oxohexa-μ-carboxylates (basic zinc carboxylates)," *Can. J. Chem.*, v. 61, pp. 1218-1221.
He, C.-T. et al. (2013) "A Porous Coordination Framework for Highly Sensitive and Selective Solid-Phase Microextraction of Non-Polar Volatile Organic Compounds," *Chem. Sci.*, v.4(1), pp. 351-356.
Heering, C. et al. (2013) "Electronic Supplementary Information (ESI) Bifunctional Pyrazolate-Carboxylate Ligands for Isoreticular Cobalt and Zinc M0F-5 Analogs with Magnetic Analysis of the {Co4(4-0)} Node," URL: http://www.rsc.org/suppdata/ce/c3/C3ee41426d/c3ce41426d.pdf.
Heering, C. et al. (2013) "Bifunctional Pyrazolate-Carboxylate Ligands for Isoreticular Cobalt and Zinc M0F-5 Analogs with Magnetic Analysis of the {Co4([mu]4-0)} Node," *Cryst. Eng. Comm.*, v.15(45), pp. 9757-9768.
Padial, N. M. (2013) "Highly Hydrophobic Isoreticular Porous Metal-Organic Frameworks for the Capture of Harmful Volatile Organic Compounds," *Angewandte Chemie Int'l Ed.*, v.52(32), pp. 8290-8294.
Torres-Knoop, A. et al. (2014) "Separating Xylene Isomers by Commensurate Stacking of p-Xylene within Channels of MAF-X8†," *Angew. Chemie.*, v.53(30), pp. 7774-7778.
Ye, Z.-M. et al. (2017) "A New Isomeric Porous Coordination Framework Showing Single-Crystal to Single-Crystal Structural Transformation and Preferential Adsorption of 1,3-Butadiene from C4 Hydrocarbons," *Cryst. Growth Des.*, v. 17(4), pp. 2166-2171.
Dechnik, Janina, et al., Mixed-Matrix Membranes of the Air-Stable MOF-5 Analogue [Co4(μ 4-O)(Me2pzba)3] with a Mixed-Functional Pyrazolate-Carboxylate Linker for CO2/CH4 Separation, Crystal Growth & Design, American Chemical Society, 2017, pp. 4090-4099, vol. 17.
Ye, Zi-Ming, et al., A New Isomeric Porous Coordination Framework Showing Single-Crystal to Single-Crystal Structural Transformation and Preferential Adsorption of 1,3-Butadiene from C4 Hydrocarbons, Crystal Growth & Design, American Chemical Society, 2017, pp. 2166-2171, vol. 17.
He, Chun-Ting, et al., A porous coordination framework for highly sensitive and selective solid-phase microextraction of non-polar volatile organic compounds†, RSC Publishing, Chemical Science, 2013, pp. 351-356, vol. 4.
Torres-Knoop, Ariana, et al., Separating Xylene Isomers by Commensurate Stacking of p-Xylene within Channels of MAF-X8, Angewandte Communications, 2014, pp. 7774-7778, vol. 53.

\* cited by examiner

METAL-ORGANIC FRAMEWORK MATERIALS COMPRISING A PYRAZOLYLBENZOATE LIGAND AND METHODS FOR PRODUCTION THEREOF

CROSS-REFERENCE TO RELATED APPLICATIONS

This application is a national stage application under 35 USC 371 of International Application No. PCT/US2020/034486 filed on May 26, 2020, which claimed the benefit of U.S. Provisional Patent Application No. 62/870,188 filed Jul. 3, 2019.

FIELD

The present disclosure relates to metal-organic framework materials (MOFs) formed from a pyrazolylbenzoate ligand.

BACKGROUND

MOFs are a relatively new class of highly porous network materials. In contrast to zeolites, which are purely inorganic in character, MOFs comprise metal ions or clusters interconnected by multidentate organic ligands that function as "struts" bridging the metal ions or clusters together in an extended one-, two-, or three-dimensional coordination network structure (e.g., as a coordination polymer). MOFs offer a high degree of structural and functional tunability which result from the ability to modulate and control their structure and porosity. Such features are not generally available with other conventional porous materials. MOFs are characterized by low densities, high internal surface areas, and pores and channels that are tunable through selection of the multidentate organic ligand and the metal or metal source used during synthesis.

MOF-5, also known as IRMOF-1, having a general formula of $Zn_4O(1,4\text{-benzenedicarboxylate})_3$, is the prototypical example of a MOF and was developed nearly 20 years ago. This material and its isoreticular materials (i.e., materials having the same topology) exhibit high pore volumes and high surface areas and have been explored for use in applications taking advantage of these features. However, the long-term performance and stability of these MOFs under ambient moisture conditions has not been reliably established.

MOFs have been investigated extensively for applications in gas storage, gas and liquid separation, sensing, catalysis, drug delivery, and waste remediation, among others. The wide array of potential applications for MOFs stems from the nearly infinite combination of multidentate organic ligands and metal sources available for synthesizing MOFs. In particular, the prospective ability to control the porosity, composition, and functionality of MOFs through selection of components, functionalization, or post-synthetic modifications, makes MOFs promising candidates towards providing stable materials specifically designed for specific applications.

SUMMARY

In some embodiments, the present disclosure provides MOFs comprising a plurality of metal clusters comprising a $M_4O$ cluster, wherein M is a metal, and a plurality of multidentate organic ligands coordinated to the plurality of metal clusters to define an at least partially crystalline network structure having a plurality of internal pores, the multidentate organic ligand comprising 4-(1H-pyrazol-4-yl)benzoate.

In some or other embodiments, methods for synthesizing MOFs may comprise: combining a metal source with 4-(1H-pyrazol-4-yl)benzoic acid; and reacting the metal source with the 4-(1H-pyrazol-4-yl)benzoic acid to form a MOF having an at least partially crystalline network structure with a plurality of internal pores defined therein and comprising a plurality of metal clusters coordinated to a multidentate organic ligand comprising 4-(1H-pyrazol-4-yl)benzoate, and the plurality of metal clusters comprising one or more $M_4O$ clusters, wherein M is a metal.

In some or other embodiments, the present disclosure provides methods for the sorptive uptake of a chemical species. The method comprises contacting a mixture comprising one or more chemical species with a metal-organic framework material comprising a plurality of metal clusters comprising one or more $M_4O$ clusters, wherein M is a metal, and a plurality of multidentate organic ligands coordinated to the plurality of metal clusters to define an at least partially crystalline network structure having a plurality of internal pores, the multidentate organic ligand comprising 4-(1H-pyrazol-4-yl)benzoate and/or 4-(3,5-dimethyl-1H-pyrazol-4-yl)benzoate; and sorbing at least a portion of the one or more chemical species into at least a portion of the internal pores.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one of ordinary skill in the art and having the benefit of this disclosure.

DETAILED DESCRIPTION

Figure 1:
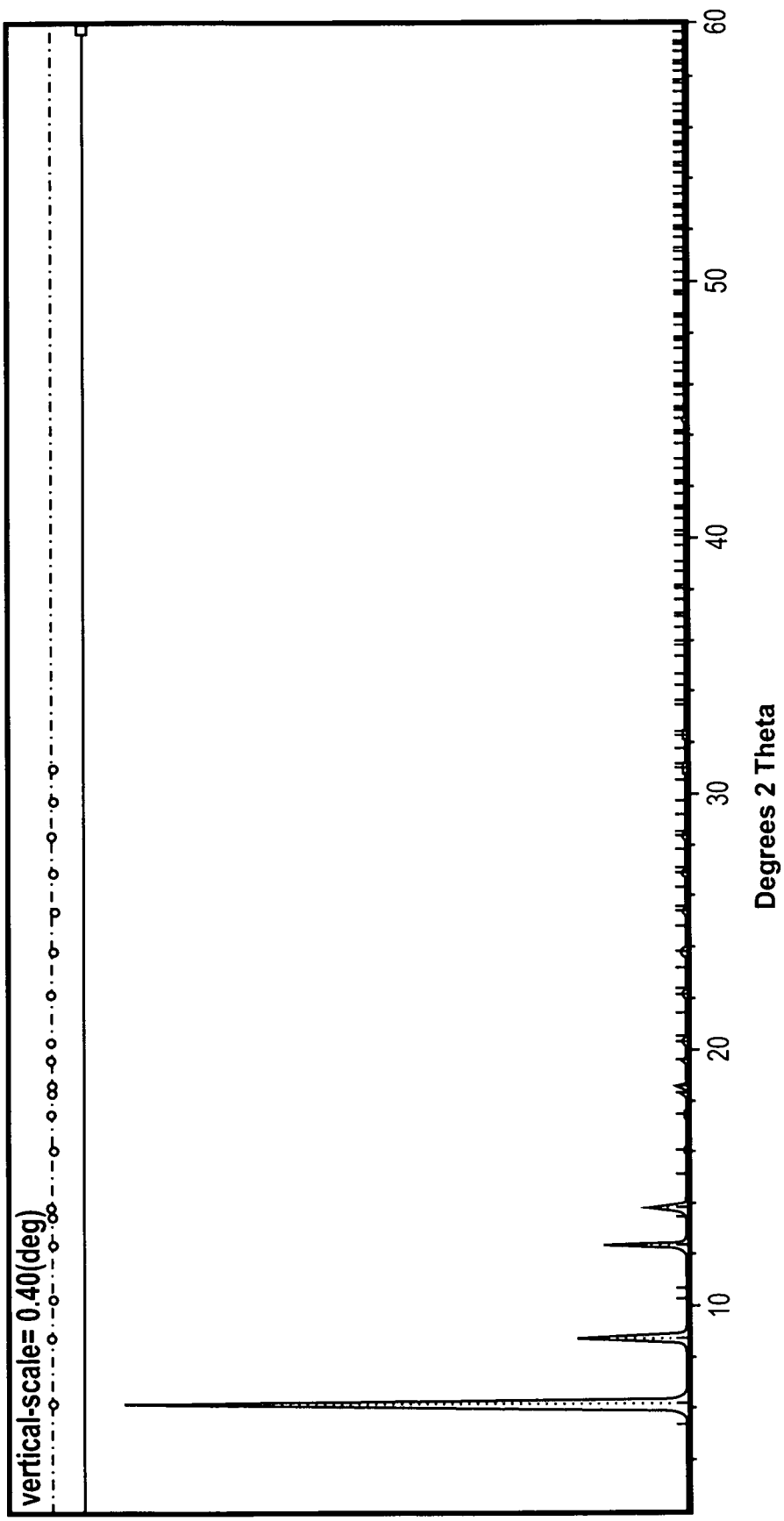
FIG. 1 shows an x-ray powder diffraction pattern for the MOF obtained in Example 1.

The present disclosure relates to MOFs formed from a pyrazolylbenzoate ligand.

As discussed in brief above, MOFs may be synthesized by reacting a multidentate organic ligand with a suitable metal source to form a crystalline or partially crystalline network structure having a plurality of internal pores. The network structure may constitute a coordination polymer in some instances. The structure and properties of MOFs are tunable through selection of the multidentate organic ligand and the metal or metal source. As highly porous materials, MOFs can selectively adsorb and/or separate different types of gases, molecules or other chemical entities. As such, MOFs have potential applications including gas storage and separation. However, the chemical stability of many conventional MOFs hamper the ability to take advantage of their porous structure.

The present disclosure provides MOFs comprising multidentate organic ligands that are readily available and possess differing binding sites. In particular, the multidentate organic ligands employed in the present disclosure comprise a pyrazolyl moiety as a first binding site and carboxylate moiety as a second binding site, which are linked together via a phenyl group. The pyrazolyl and phenyl moieties of the multidentate organic ligands may include various substituents. Surprisingly, the multidentate organic ligands described herein may afford network structures having the topology of MOF-5 with a crystalline structure in the Fm3m space group and exhibit increased stability under ambient conditions compared to MOF-5.

In particular embodiments, the multidentate organic ligands of the present disclosure may comprise 4-(1H-pyrazol-4-yl)benzoate. As discussed further herein, this multidentate organic ligand may react with various metal sources to form MOFs having advantageous properties. More specific examples of such MOFs may comprise a plurality of zinc clusters and a 4-(1H-pyrazol-4-yl)benzoate multidentate organic ligand coordinated to the plurality of zinc clusters via at least one binding site to define an at least partially crystalline network structure having a plurality of internal pores.

Surprisingly, 4-(1H-pyrazol-4-yl)benzoate and similar multidentate organic ligands may form MOFs having variable network structures depending upon the metal source that is used. In some instances, a preformed metal cluster, such as $Zn_4O(2,2-dimethylbutanote)_6$ ($Zn_4O(DMBA)_6$) or similar metal carboxylate clusters, may be particularly suitable for reaction with the foregoing pyrazolylbenzoate ligand to form MOFs. While preformed metal clusters may be particularly desirable metal sources for promoting formation of MOFs, other metal sources may also be satisfactorily used. The ability of the pyrazolylbenzoate ligand described herein to form stable MOFs is believed to result from structural strength of the robust metal-ligand bonding, while still positioning the binding sites effectively to promote large cubic, pores via coordination of metal centers to the pyrazolate and carboxylate moieties.

In addition to the foregoing, MOFs synthesized using the multidentate organic ligands described herein may undergo exchange with other metals to replace at least a portion of the metal atoms at the metal centers with one or more different metals. The metal centers may be defined by one or more metal clusters in some cases. The one or more different metals may be introduced for any purpose, such as for conveying additional structural stabilization or for promoting a catalytic reaction. Minimal structural reorganization occurs when metal exchange takes place in many cases.

Before describing the various embodiments of the present disclosure in further detail, a listing of terms follows to aid in better understanding the present disclosure.

All numerical values within the detailed description and the claims herein are modified by "about" or "approximately" with respect to the indicated value, and take into account experimental error and variations that would be expected by a person having ordinary skill in the art. Unless otherwise indicated, room temperature is about 25° C.

As used in the present disclosure and claims, the singular forms "a," "an," and "the" include plural forms unless the context clearly dictates otherwise.

The term "and/or" as used in a phrase such as "A and/or B" herein is intended to include "A and B," "A or B," "A", and "B."

For the purposes of the present disclosure, the new numbering scheme for groups of the Periodic Table is used. In said numbering scheme, the groups (columns) are numbered sequentially from left to right from 1 through 18, excluding the f-block elements (lanthanides and actinides).

As used in the present disclosure and claims, Me is methyl, Et is ethyl, Pr is propyl, cPr is cyclopropyl, nPr is n-propyl, iPr is isopropyl, Bu is butyl, nBu is normal butyl, iBu is isobutyl, sBu is sec-butyl, tBu is tert-butyl, Cy is cyclohexyl, Oct is octyl, Ph is phenyl, and Bn is benzyl, The term "hydrocarbon" refers to a class of compounds having hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different numbers of carbon atoms. The term "$C_n$" refers to hydrocarbon(s) or a hydrocarbyl group having n carbon atom(s) per molecule or group, wherein n is a positive integer. Such hydrocarbon compounds may be one or more of linear, branched, cyclic, acyclic, saturated, unsaturated, aliphatic, or aromatic, with optional substitution being present in some cases.

The terms "hydrocarbyl" and "hydrocarbyl group" are used interchangeably herein. The term "hydrocarbyl group" refers to any $C_1$-$C_{100}$ hydrocarbon group bearing at least one unfilled valence position when removed from a parent compound. Suitable "hydrocarbyl" and "hydrocarbyl groups" may be optionally substituted. The term "hydrocarbyl group having 1 to about 100 carbon atoms" refers to an optionally substituted moiety selected from a linear or branched $C_1$-$C_{100}$ alkyl, a $C_3$-$C_{100}$ cycloalkyl, a $C_6$-$C_{100}$ aryl, a $C_2$-$C_{100}$ heteroaryl, a $C_1$-$C_{100}$ alkylaryl, a $C_7$-$C_{100}$ arylalkyl, and any combination thereof.

The term "substituted" refers to replacement of at least one hydrogen atom or carbon atom of a hydrocarbon or hydrocarbyl group with a heteroatom or heteroatom functional group. Heteroatoms may include, but are not limited to, B, O, N, S, P, F, Cl, Br, I, Si, Pb, Ge, Sn, As, Sb, Se, and Te. Heteroatom functional groups that may be present in substituted hydrocarbons or hydrocarbyl groups include, but are not limited to, functional groups such as O, S, S=O, $S(=O)_2$, $NO_2$, F, Cl, Br, I, $NR_2$, OR, SeR, TeR, $PR_2$, $AsR_2$, $SbR_2$, SR, $BR_2$, $SiR_3$, $GeR_3$, $SnR_3$, $PbR_3$, where R is a hydrocarbyl group or H. Suitable hydrocarbyl R groups may include alkyl, alkenyl, alkynyl, aryl, heteroaryl, cycloalkyl, heterocyclyl, and the like, any of which may be optionally substituted.

The term "optionally substituted" means that a hydrocarbon or hydrocarbyl group may be unsubstituted or substituted. For example, the term "optionally substituted hydrocarbyl" refers to replacement of at least one hydrogen atom or carbon atom in a hydrocarbyl group with a heteroatom or heteroatom functional group. Unless otherwise specified, any of the hydrocarbyl groups herein may be optionally substituted.

The terms "linear" or "linear hydrocarbon" refer to a hydrocarbon or hydrocarbyl group having a continuous carbon chain without side chain branching, in which the continuous carbon chain may be optionally substituted.

The terms "cyclic" or "cyclic hydrocarbon" refer to a hydrocarbon or hydrocarbyl group having a closed carbon ring, which may be optionally substituted.

The terms "branched" or "branched hydrocarbon" refer to a hydrocarbon or hydrocarbyl group having a linear carbon chain or a closed carbon ring, in which a hydrocarbyl side chain extends from the linear carbon chain or the closed carbon ring. Optional substitution may be present in the linear carbon chain, the closed carbon ring, and/or the hydrocarbyl side chain.

The terms "saturated" or "saturated hydrocarbon" refer to a hydrocarbon or hydrocarbyl group in which all carbon atoms are bonded to four other atoms, with the exception of an unfilled valence position being present upon a carbon atom in a hydrocarbyl group.

The terms "unsaturated" or "unsaturated hydrocarbon" refer to a hydrocarbon or hydrocarbyl group in which one or more carbon atoms are bonded to less than four other atoms, exclusive of an open valence position upon carbon being present. That is, the term "unsaturated" refers to a hydrocarbon or hydrocarbyl group bearing one or more double and/or triple bonds, with the double and/or triple bonds being between two carbon atoms and/or between a carbon atom and a heteroatom.

The terms "aromatic" or "aromatic hydrocarbon" refer to a hydrocarbon or hydrocarbyl group having a cyclic arrangement of conjugated pi-electrons that satisfies the Hückel rule.

The term "alkyl" refers to a hydrocarbyl group having no unsaturated carbon-carbon bonds, and which may be optionally substituted.

The terms "alkene" and "olefin" are used synonymously herein. Similarly, the terms "alkenic" and "olefinic" are used synonymously herein. Unless otherwise noted, all possible geometric isomers are encompassed by these terms.

The term "aryl" is equivalent to the term "aromatic" as defined herein. The term "aryl" refers to both aromatic compounds and heteroaromatic compounds, which may be optionally substituted. Both mononuclear and polynuclear aromatic compounds are encompassed by these terms.

The terms "heteroaryl" and "heteroaromatic" refer to an aromatic ring containing a heteroatom and which satisfies the Hückel rule.

Examples of aromatic hydrocarbyl groups include, but are not limited to, phenyl, tolyl, xylyl, naphthyl, and the like. Heteroaryl and polynuclear heteroaryl groups may include, but are not limited to, pyridyl, quinolinyl, isoquinolinyl, pyrimidinyl, quinazolinyl, acridinyl, pyrazinyl, quinoxalinyl, imidazolyl, benzimidazolyl, pyrazolyl, benzopyrazolyl, oxazolyl, benzoxazolyl, isoxazolyl, benzisoxazolyl, imidazolinyl, thiophenyl, benzothiophenyl, furanyl and benzofuranyl. Polynuclear aryl groups may include, but are not limited to, naphthalenyl, anthracenyl, indanyl, indenyl, and tetralinyl.

As used herein, the term "multidentate" refers to a compound having two or more potential sites for coordinating a metal center. Accordingly, the term "multidentate" encompasses bidentate, tridentate, tetradentate, and higher denticity ligands.

The term "metal center" refers to a single metal atom or metal ion, or a group of metal atoms or metal ions to which a ligand is coordinatively bonded.

The term "metal cluster" refers to a group of metal atoms or metal ions to which a ligand is coordinatively bonded.

The term "secondary building unit" refers to a metal cluster to which two or more multidentate ligands are coordinatively bonded. For example, a secondary building unit may have the formula $M_4O$ and may be coordinated to multidentate ligands, such as carboxylate groups, to form MOFs having multi-metal nuclear carboxylate clusters of formula $M_4O(CO_2)_6$. The cluster $M_4O$ may also be coordinated by bidentate groups including carboxylate or hydrazyl groups to form MOFs.

The term "preformed metal cluster" refers to a grouping of multiple metal atoms and one or more ligands, in which the grouping is synthesized prior to being combined with another material to form a MOF.

The term "at least partially crystalline" means that a substance exhibits an x-ray powder diffraction pattern.

The term "binding site" refers to a chemical entity capable of coordinating a metal center by a metal-ligand bond.

Accordingly, MOFs of the present disclosure may comprise: a plurality of metal centers and a plurality of multidentate organic ligands coordinated to the plurality of metal centers to define an at least partially crystalline network structure having a plurality of internal pores. The multidentate organic ligands comprise 4-(1H-pyrazol-4-yl)benzoate.

In more specific examples, the MOFs described herein may comprise a plurality of metal clusters comprising $M_4O$ clusters (M is a metal), and a plurality of multidentate organic ligands coordinated to the plurality of metal clusters to define an at least partially crystalline network structure having a plurality of internal pores. The multidentate organic ligands comprise 4-(1H-pyrazol-4-yl)benzoate.

Formula 1 below shows the chemical structure of 4-(1H-pyrazol-4-yl)benzoic acid, which is capable of becoming incorporated in MOFs of the present disclosure as a multidentate organic ligand.

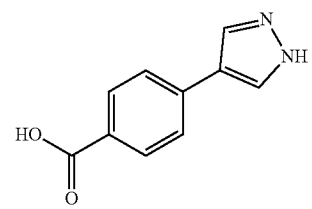

Formula 1

Formula 2 below shows the chemical structure of 4-(3,5-dimethyl-1H-pyrazol-4-yl)benzoic acid, which is also capable of becoming incorporated in MOFs of the present disclosure as a multidentate organic ligand.

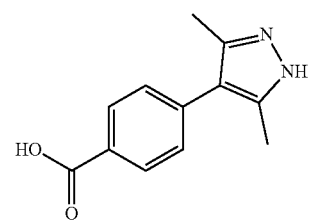

Formula 2

The identity of the metal centers or metal clusters that may be present in the MOFs disclosed herein is not considered to be particularly limited. In some embodiments, at least a portion of the plurality of metal centers or metal clusters may comprise metals having a tetrahedral geometry. In some embodiments, at least a portion of the plurality of metal centers or metal clusters may comprise a divalent metal. Trivalent metals may also be suitably included in some instances, either alone or in combination with one or more divalent metals. Suitable divalent metals that may be present in the MOFs disclosed herein include, for example, zinc, cobalt, nickel, copper, iron, chromium, manganese, or any combination thereof. The metal(s) comprising the plurality of metal centers or metal clusters may be introduced when reacting a suitable metal source with the multidentate organic ligands disclosed above, or at least a portion of the metal(s) in the metal centers or metal clusters may be introduced via an exchange reaction after forming the at least partially crystalline network structure defining the MOF. In some embodiments, the plurality of metal centers or metal clusters may be in the form of $M_4O$ secondary building units.

In some embodiments, suitable metal salts that may be used to form MOFs according to the disclosure herein include metal ions such as, but not limited to, $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Mo^{3+}$, $W^{3+}$ $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$ $Rh^+$, $Ir^{2+}$, $Ir^+$, $Ni^{2+}$, $Ni^+$, $Pd^{2+}$, $Pd^+$, $Pt^{2+}$, $Pt^+$, $Cu^{2+}$, $Cu^+$, $Ag^+$, $Au^+$, $Zn^{2+}$, $Cd^{2+}$, $Hg^{2+}$, $Al^{3+}$, $Ga^{3+}$, $In^{3+}$, $Ti^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^+$, $Sb^{5+}$, $Sb^{3+}$, $Sb^+$, $Bi^{5+}$, $Bi^{3+}$ and $Bi^+$. Other oxidation states of these metal ions may also be suitably used in some instances. Depending on the identity of the multidentate organic ligand and the conditions under which the MOF is formed, suitable counterion forms for the metal ions may include, but are not limited to, nitrate, nitrite, sulfate, hydrogen sulfate, oxide, acetate, formate, oxide, hydroxide, benzoate, alkoxide, carbonate, acetylacetonoate, hydrogen carbonate, fluoride, chloride, bromide, iodide, phosphate, hydrogen phosphate, dihydrogen phosphate, or the like.

In other particular examples, a preformed metal cluster may comprise a suitable metal source for forming the MOFs disclosed herein. Although preformed metal clusters may be particularly desirable for use in forming the MOFs of the present disclosure, it is to be appreciated that common metal salts may be suitable in certain instances as well, as specified above. For example, metal oxides and metal carboxylates (e.g., metal acetates) may also be suitably used to form MOFs having a network structure related to that produced when using a preformed metal cluster. Determination of the presence of a network structure and crystallinity thereof, including a determination of whether a particular network structure is related to another network structure, may be performed by x-ray powder diffraction, as described elsewhere herein. One example of a suitable metal cluster that may be used to promote formation of a MOF with the multidentate organic ligands described herein is a zinc cluster described by the formula $Zn_4O(2,2\text{-dimethylbutanoic acid})_6$ ($Zn_4O(DMBA)_6$).

Accordingly, still more specific MOFs of the present disclosure may comprise a plurality of metal clusters, and 4-(1H-pyrazol-4-yl)benzoate coordinated to the plurality of metal clusters to define an at least partially crystalline network structure having a plurality of internal pores. In yet still more specific examples, such MOFs may comprise a plurality of zinc clusters, and 4-(1H-pyrazol-4-yl)benzoate coordinated to the plurality of zinc clusters to define an at least partially crystalline network structure having a plurality of internal pores. In some embodiments, the MOFs may further comprise a residual ligand, a metal salt, or a solvent incorporated within at least a portion of the plurality of internal pores in the network structure, with 2,2-dimethylbutanoic acid, a salt thereof, or another carboxylic acid/carboxylate salt being representative examples of such residual ligands. In some or other more specific embodiments, the MOFs of the present disclosure comprising a plurality of zinc clusters may further comprise a plurality of nickel centers also coordinated to the 4-(1H-pyrazol-4-yl) benzoate ligand via at least one binding site.

The MOFs formed according to the disclosure herein may be characterized in terms of their internal porosity, particularly MOFs formed from 4-(1H-pyrazol-4-yl)benzoate as a multidentate organic ligand. The MOFs of the present disclosure may include micropores, mesopores, macropores and any combination thereof. Micropores are defined herein as having a pore size of about 2 nm or below, and mesopores are defined herein as having a pore size from about 2 nm to about 50 nm. Determination of microporosity and/or mesoporosity may be determined by analysis of the nitrogen adsorption isotherms at 77 K, as will be understood by one having ordinary skill in the art. Internal pore volumes and other morphological features of the MOFs may similarly be determined from the nitrogen adsorption isotherms, as also will be understood by one having ordinary skill in the art. For a typical material formed according to the disclosure herein, pore diameters may range from about 10 Å to about 20 Å as determined by DFT fitting of the $N_2$ adsorption isotherms conducted at 77 K, and pore volumes from about 0.9 cc/g to about 1.5 cc/g are obtainable. Further, total surface areas from about 2800 $m^2/g$ to about 3700 $m^2/g$ are achievable.

Methods are also described herein for synthesizing the MOFs of the present disclosure. Some syntheses may be advantageously conducted with a preformed metal cluster as a metal source, as discussed above, but other metal sources, including some simple metal salts may also be used suitably as well. Advantageously, the metal source may be selected such that MOFs having related, but slightly different network structures, are obtained. As such, selection of the metal source used for synthesizing the MOFs disclosed herein may allow tailoring of the network structure to be realized for compatibility with particular applications. In some instances, a metal source suitable for forming a metal cluster in the MOFs may be used.

Accordingly, certain methods of the present disclosure may comprise: combining a metal source with 4-(1H-pyrazol-4-yl)benzoic acid, and reacting the metal source with the 4-(1H-pyrazol-4-yl)benzoic acid to form a metal-organic framework material having an at least partially crystalline network structure with a plurality of internal pores defined therein and comprising a plurality of metal centers or metal clusters coordinated to a multidentate organic ligand comprising 4-(1H-pyrazol-4-yl)benzoate. The plurality of metal clusters may comprise one or more MAO clusters, wherein M is a metal. In more specific embodiments, the metal source may be a preformed metal cluster, such as a preformed metal cluster comprising zinc, and more particularly $Zn_4O(2,2\text{-dimethylbutanoate})_6$ or a similar metal carboxylate cluster.

Other suitable zinc sources for forming MOFs when using 4-(1H-pyrazol-4-yl)benzoate as a multidentate organic ligand include, for example, zinc nitrate and zinc acetate. Both of these metal sources may promote formation of a MOF having a network structure related to that formed in the presence of $Zn_4O(2,2\text{-dimethylbutanoic acid})_6$.

Some or other methods of the present disclosure may comprise thermally or chemically removing the residual ligand, the metal salt, the solvent, or any combination thereof that may be present in the plurality of internal pores of the MOF. For example, 2,2-dimethylbutanoic acid, a salt thereof, another carboxylic acid/carboxylate salt, zinc salt, or dimethylformamide, if present, may be thermally removed from the internal pores of the MOF.

Some or other methods of the present disclosure may comprise exchanging at least a portion of a first metal comprising the plurality of metal centers or metal clusters for a second metal. For example, at least a portion of zinc atoms comprising the metal centers may be exchanged for nickel atoms, according to various embodiments of the present disclosure. Metal exchange may be affected by contacting the MOFs with a salt solution, for example.

Embodiments disclosed herein include:

A. MOFs having a 4-(1H-pyrazol-4-yl)benzoate scaffold. The MOFs comprise: a plurality of metal clusters comprising one or more $M_4O$ clusters, wherein M is a metal; and a plurality of multidentate organic ligands coordinated to the plurality of metal clusters to define an at least partially crystalline network structure having a plurality of internal pores, the multidentate organic ligand comprising 4-(1H-pyrazol-4-yl)benzoate.

B. MOFs having a 4-(1H-pyrazol-4-yl)benzoate scaffold and comprising zinc. The MOFs comprise: a plurality of metal clusters comprising one or more $M_4O$ clusters, wherein M is a metal; and a plurality of multidentate organic ligands coordinated to the plurality of metal clusters to define an at least partially crystalline network structure having a plurality of internal pores, the multidentate organic ligand comprising 4-(1H-pyrazol-4-yl)benzoate, wherein at least a portion of the plurality of metal clusters comprise zinc.

C. Methods for making a MOF having a 4-(1H-pyrazol-4-yl)benzoate scaffold. The methods comprise: combining a metal source with 4-(1H-pyrazol-4-yl)benzoic acid; and reacting the metal source with the 4-(1H-pyrazol-4-yl)benzoic acid to form a metal-organic framework material having an at least partially crystalline network structure with a plurality of internal pores defined therein and comprising a plurality of metal clusters coordinated to a multidentate organic ligand comprising 4-(1H-pyrazol-4-yl)benzoate, the plurality of metal clusters comprising one or more $M_4O$ clusters, wherein M is a metal.

D. Methods for making a MOF having a 4-(1H-pyrazol-4-yl)benzoate and zinc. The methods comprise: combining a metal source with 4-(1H-pyrazol-4-yl)benzoic acid; and reacting the metal source with the 4-(1H-pyrazol-4-yl)benzoic acid to form a metal-organic framework material having an at least partially crystalline network structure with a plurality of internal pores defined therein and comprising a plurality of metal clusters coordinated to a multidentate organic ligand comprising 4-(1H-pyrazol-4-yl)benzoate, wherein the metal source comprises a preformed metal cluster, and the preformed metal cluster comprises zinc.

E. Gas sorption methods. The methods comprise: contacting a mixture comprising one or more chemical species with a metal-organic framework material comprising: a plurality of metal clusters comprising one or more $M_4O$ clusters, wherein M is a metal, and a plurality of multidentate organic ligands coordinated to the plurality of metal centers to define an at least partially crystalline network structure having a plurality of internal pores, the multidentate organic ligand comprising 4-(1H-pyrazol-4-yl)benzoate and/or 4-(3,5-dimethyl-1H-pyrazol-4-yl)benzoate; and sorbing at least a portion of the one or more chemical species into at least a portion of the internal pores.

Embodiments A-E may have one or more of the following additional elements in any combination:

Element 1: wherein at least a portion of the plurality of metal clusters has a tetrahedral geometry.

Element 2: wherein at least a portion of the plurality of metal clusters comprise a divalent metal.

Element 3: wherein at least a portion of the plurality of metal clusters comprise zinc, cobalt, nickel, copper, iron, chromium, manganese, or any combination thereof.

Element 4: wherein the at least partially crystalline network structure exhibits an x-ray powder diffraction pattern consistent with a cubic space group.

Element 5: wherein the metal-organic framework material is a reaction product of a preformed metal cluster and the 4-(1H-pyrazol-4-yl)benzoate.

Element 6: wherein the plurality of metal clusters are formed from preformed metal clusters.

Element 7: wherein the preformed metal clusters comprise $Zn_4O(2,2\text{-dimethylbutanoate})_6$.

Element 8: wherein the internal pores have pore diameters in a range of about 10 Å to about 20 Å as determined by DFT fitting of the $N_2$ adsorption isotherms conducted at 77K.

Element 9: wherein the internal pores have a pore volume in a range of about 0.9 cc/g to about 1.5 cc/g.

Element 10: wherein the at least partially crystalline network structure has a BET surface area in a range of about 2800 $m^2/g$ to about 3700 $m^2/g$.

Element 11: wherein the at least partially crystalline network structure has an x-ray powder diffraction pattern having characteristic peaks of at least 6.21, 8.76, 12.40, and 13.83 (all ±5%) degree 2-theta (°2θ).

Element 12: wherein the metal source is a preformed metal cluster.

Element 13: wherein the plurality of metal clusters define a plurality of metal centers, the method further comprising: exchanging at least a portion of a first metal comprising the plurality of metal centers for a second metal.

Element 14: wherein the one or more chemical specie comprises methane.

By way of non-limiting example, exemplary combinations applicable to A include 1 and 2; 1 and 3; 1 and 4; 1 and 5; 1 and 6; 1 and 8; 1 and 9; 1 and 10; 1 and 11; 2 and 3; 2 and 4; 2 and 5; 2 and 6; 2 and 8; 2 and 9; 2 and 10; 2 and 11; 3 and 4; 3 and 5; 3 and 6; 3 and 8; 3 and 9; 3 and 10; 3 and 11; 4 and 5; 4 and 6; 4 and 8; 4 and 9; 4 and 10; 4 and 11; 5 and 6; 5 and 8; 5 and 9; 5 and 10; 5 and 11; 6 and 7; 6 and 8; 6 and 9; 6 and 10; 6 and 11; 6, 7 and 8; 6, 7, and 9; 6, 7, and 10; 6, 7 and 11; 8 and 9; 8 and 10; 8 and 11; 9 and 10; 9 and 11; 10 and 11.

Exemplary combinations applicable to B include 1 and 2; 1 and 3; 1 and 4; 1 and 5; 1 and 6; 1 and 8; 1 and 9; 1 and 10; 1 and 11; 2 and 3; 2 and 4; 2 and 5; 2 and 6; 2 and 8; 2 and 9; 2 and 10; 2 and 11; 3 and 4; 3 and 5; 3 and 6; 3 and 8; 3 and 9; 3 and 10; 3 and 11; 4 and 5; 4 and 6; 4 and 8; 4 and 9; 4 and 10; 4 and 11; 5 and 6; 5 and 8; 5 and 9; 5 and 10; 5 and 11; 6 and 7; 6 and 8; 6 and 9; 6 and 10; 6 and 11; 6, 7 and 8; 6, 7, and 9; 6, 7, and 10; 6, 7 and 11; 8 and 9; 8 and 10; 8 and 11; 9 and 10; 9 and 11; 10 and 11.

Exemplary combinations applicable to C include 1 and 12; 1 and 13.

Exemplary combinations applicable to D include 7 and 13.

To facilitate a better understanding of the embodiments described herein, the following examples of various representative embodiments are given. In no way should the following examples be read to limit, or to define, the scope of the present disclosure.

Examples x-Ray powder diffraction patterns in the examples below were obtained using Cu K-α radiation.

BET surface areas in the examples below were determined from $N_2$ adsorption isotherms obtained at 77 K. $N_2$ adsorption isotherms were measured using a Tristar II analyzer (Micromeritics) at 77 K. Before measurement, the samples were degassed at 150° C. to a constant pressure of $10^{-5}$ torr for 4 hours. The surface area was then measured by the amount of $N_2$ adsorbed onto the surface of the sample.

Regression analysis was subsequently applied to the data, resulting in an isotherm. The isotherms were further analyzed to calculate the micropore volume and other quantities.

Example 1: Metal-Organic Framework Synthesis. 4-(1H-pyrazol-4-yl)benzoic acid (720 mg) was dissolved in 100 mL of a 30 vol. % solution of water in N,N-dimethylformamide (DMF). To this solution was added 1.434 g $Zn_4O$ (2,2-dimethylbutanoate)$_6$ (2,2-dimethylbutanoate=DMBA). Synthesis of $Zn_4O(DMBA)_6$ was accomplished by literature methods described in M. R. Gordon, et al., "Preparation and properties of tetrazine $\mu_4$-oxohexa-$\mu$-carboxylates (basic zinc carboxylates)," Can. J. Chem., 1983, pp. 1218-1221, 61. The reaction mixture was stirred at 60° C. for 16 hours, after which the solids were isolated via centrifugation. The solids were washed with benzene. The product was then freeze-dried.

Example 2: Product Characterization. FIG. 1 shows an x-ray powder diffraction pattern for the product obtained in Example 1. As shown, a highly crystalline material was obtained when using $Zn_4O(DMBA)_6$ as the zinc source in combination 4-(1H-pyrazol-4-yl)benzoic acid. Table 1 lists the 2-theta values (°), d-spacing (Å), and relative intensity H (%) of the x-ray powder diffraction peaks of the product obtained in Example 1.

TABLE 1

| 2-theta (°) | d (Å) | H (%) |
|---|---|---|
| 6.213 | 14.2149 | 100 |
| 8.76 | 10.086 | 18 |
| 10.279 | 8.5993 | 0.3 |
| 12.395 | 7.1354 | 13 |
| 13.51 | 6.5489 | 0.6 |
| 13.833 | 6.3964 | 6 |
| 15.143 | 5.8462 | 0.1 |
| 16.078 | 5.508 | 0.4 |
| 17.53 | 5.0552 | 0.6 |
| 18.326 | 4.8373 | 0.9 |
| 18.584 | 4.7707 | 1.5 |
| 19.606 | 4.5242 | 0.4 |
| 20.298 | 4.3715 | 0.5 |
| 20.526 | 4.3234 | 0.2 |
| 22.155 | 4.0091 | 0.5 |
| 23.224 | 3.8269 | 0.2 |
| 23.864 | 3.7257 | 0.9 |
| 24.834 | 3.5824 | 0.1 |
| 25.449 | 3.4972 | 0.3 |
| 26.413 | 3.3717 | 0.1 |
| 26.947 | 3.3061 | 0.6 |
| 28.359 | 3.1445 | 0.6 |
| 29.729 | 3.0027 | 0.1 |
| 31.034 | 2.8794 | 0.4 |
| 31.826 | 2.8094 | 0.1 |
| 32.316 | 2.768 | 0.3 |
| 33.474 | 2.6748 | 0.2 |
| 34.306 | 2.6118 | 0.1 |
| 34.674 | 2.585 | 0.1 |
| 35.846 | 2.5031 | 0.2 |
| 36.96 | 2.4302 | 0.1 |

Figure 2A:
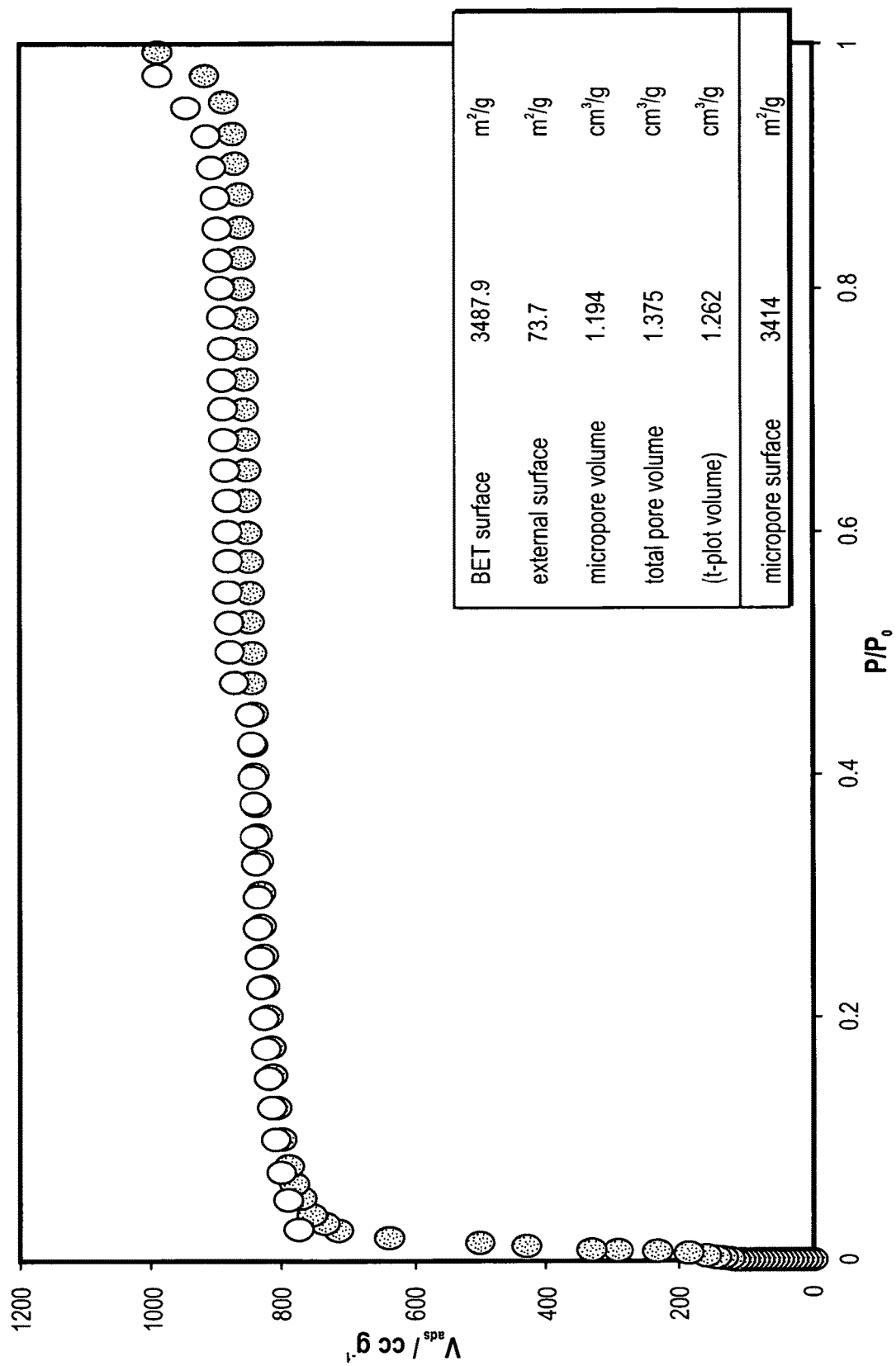
FIGS. 2A and 2B show $N_2$ adsorption isotherm at 77 K for the product of Example 1 plotted on $P/P_0$ and Log $P/P_0$ scales, respectively.
Figure 2B:
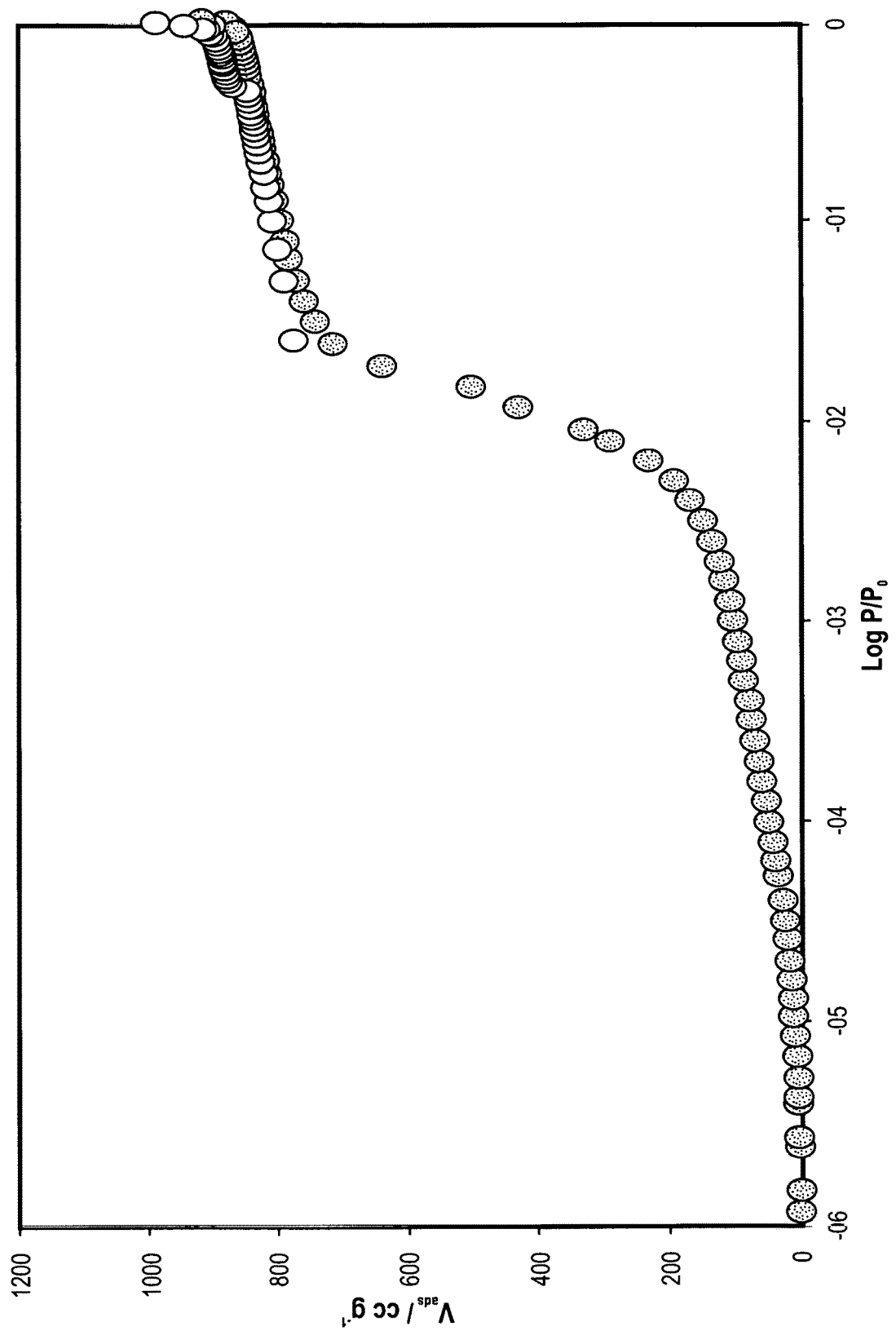

FIGS. 2A and 2B show $N_2$ adsorption isotherm at 77 K for the product of Example 1 plotted on $P/P_0$ and Log $P/P_0$ scales, respectively. The calculated BET surface area was 3487.9 $m^2/g$. The external surface was 73.7 $m^2/g$. The micropore volume was 1.194 $cm^3/g$. The corresponding total pore volume was 1.375 $cm^3/g$. The micropore surface was 3414 $m^2/g$.

Figure 3:
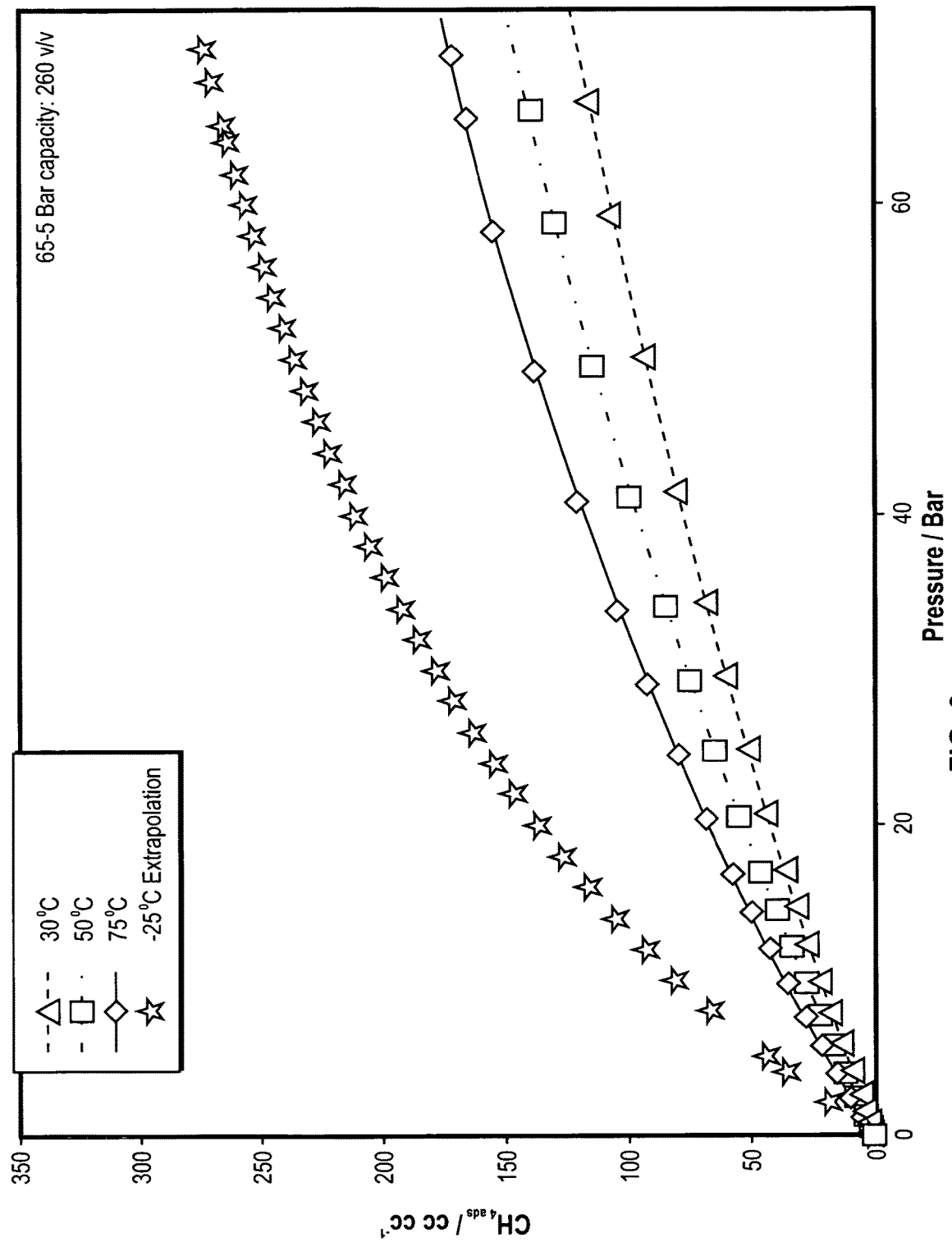
FIG. 3 shows the absolute $CH_4$ uptake for the product of Example 1 at various temperatures.

FIG. 3 shows the $CH_4$ adsorption isotherms (based on a density of 0.610 g/cc) measured at 30° C., 50° C., 75° C., and the predicted $CH_4$ adsorption isotherm at −25° C. for the product of Example 1.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. For example, the compositions described herein may be free of any component, or composition not expressly recited or disclosed herein. Any method may lack any step not recited or disclosed herein. Likewise, the term "comprising" is considered synonymous with the term "including." Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

One or more illustrative embodiments are presented herein. Not all features of a physical implementation are described or shown in this application for the sake of clarity. It is understood that in the development of a physical embodiment of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for one of ordinary skill in the art and having benefit of this disclosure.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to one having ordinary skill in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein.

The invention claimed is:

1. A metal-organic framework material comprising:
   a plurality of metal clusters comprising one or more $M_4O$ clusters, wherein M is a metal and at least a portion of the plurality of metal clusters comprise zinc; and
   a plurality of multidentate organic ligands coordinated to the plurality of metal clusters to define an at least partially crystalline network structure having a plurality of internal pores, the multidentate organic ligand comprising 4-(1H-pyrazol-4-yl)benzoate, 4-(3,5-dimethyl-1/-pyrazol-4-yl)benzoate, or a combination thereof,
   wherein the at least partially crystalline network structure has a BET surface area of about 2800 $m^2/g$ to 3700 $m^2/g$.

2. The metal-organic framework material of claim 1, wherein at least a portion of the plurality of metal clusters has a tetrahedral geometry.

3. The metal-organic framework material of claim 1, wherein at least a portion of the plurality of metal clusters further comprise cobalt, nickel, copper, iron, chromium, manganese, or any combination thereof.

4. The metal-organic framework material of claim 1, wherein the at least partially crystalline network structure exhibits an x-ray powder diffraction pattern consistent with a cubic space group.

5. The metal-organic framework material of claim 1, wherein the metal-organic framework material is a reaction product of a preformed metal cluster and the 4-(1H-pyrazol-4-yl)benzoate, the 4-(3,5-dimethyl-1H-pyrazol-4-yl)benzoate, or the combination thereof.

6. The metal-organic framework material of claim 5, wherein the preformed metal cluster comprises $Zn_4O(2,2\text{-dimethylbutanoate})_6$.

7. The metal-organic framework material of claim 1, wherein the internal pores have pore diameters in a range of about 10 Å to about 20 Å.

8. The metal-organic framework material of claim 1, wherein the internal pores have a pore volume in a range of about 0.9 cc/g to about 1.5 cc/g.

9. The metal-organic framework material of claim 1, wherein the at least partially crystalline network structure has an x-ray powder diffraction pattern having characteristic peaks of at least 6.21, 8.76, 12.40, and 13.83 (all ±5%) degree 2-theta (°2θ).

10. A method comprising:
    contacting a mixture comprising one or more chemical species with the metal-organic framework material of claim 1, and
    sorbing at least a portion of the one or more chemical species into at least a portion of the internal pores.

11. The method of claim 10, wherein the one or more chemical species comprises methane.

12. A method comprising:
    combining a metal source with 4-(1H-pyrazol-4-yl)benzoic acid, 4-(3,5-dimethyl-1H-pyrazol-4-yl)benzoate, or a combination thereof; and
    reacting the metal source with the 4-(1H-pyrazol-4-yl) benzoic acid, the 4-(3,5-dimethyl-1H-pyrazol-4-yl) benzoate, or the combination thereof to form a metal-organic framework material,
    wherein the metal source is a preformed metal cluster that comprises $Zn_4O(2,2\text{-dimethylbutanoate})_6$.

13. The method of claim 12, the method further comprising:
    exchanging at least a portion of a first metal comprising the plurality of metal clusters for a second metal.